(12) United States Patent
Wolter

(10) Patent No.: US 8,075,561 B2
(45) Date of Patent: Dec. 13, 2011

(54) BONE-FIXATION SYSTEM AND FILLER ELEMENT FOR BONE-FIXATION

(76) Inventor: Dietmar Wolter, Hoisdorf (DE)

( * ) Notice: Subject to any disclaimer, the term of this patent is extended or adjusted under 35 U.S.C. 154(b) by 1402 days.

(21) Appl. No.: 11/572,285

(22) PCT Filed: Jul. 2, 2005

(86) PCT No.: PCT/EP2005/007164
§ 371 (c)(1),
(2), (4) Date: Jan. 18, 2007

(87) PCT Pub. No.: WO2006/007965
PCT Pub. Date: Jan. 26, 2006

(65) Prior Publication Data
US 2007/0260244 A1 Nov. 8, 2007

(30) Foreign Application Priority Data
Jul. 19, 2004 (DE) .......................... 10 2004 035 546

(51) Int. Cl.
*A61B 17/56* (2006.01)
*A61B 17/58* (2006.01)
*A61B 17/80* (2006.01)
*A61F 2/30* (2006.01)

(52) U.S. Cl. ...................................................... 606/71

(58) Field of Classification Search .................. 606/294, 606/70, 28, 326; 623/18.11
See application file for complete search history.

(56) References Cited

U.S. PATENT DOCUMENTS

| 4,653,487 | A | * | 3/1987 | Maale | 606/62 |
| 5,263,987 | A | * | 11/1993 | Shah | 623/18.11 |
| 5,791,899 | A | * | 8/1998 | Sachdeva et al. | 433/173 |
| 5,808,108 | A | * | 9/1998 | Chappelow et al. | 549/335 |
| 6,102,951 | A | * | 8/2000 | Sutter et al. | 623/18.11 |
| 6,283,969 | B1 | * | 9/2001 | Grusin et al. | 606/280 |
| 6,322,562 | B1 | * | 11/2001 | Wolter | 606/62 |
| 6,547,725 | B1 | * | 4/2003 | Paolitto et al. | 600/201 |
| 2002/0183756 | A1 | * | 12/2002 | Michelson | 606/71 |
| 2006/0074421 | A1 | * | 4/2006 | Bickley et al. | 606/72 |

FOREIGN PATENT DOCUMENTS

| DE | 43 43 117 A1 | 6/1995 |
| DE | 198 58 889.5 | * 12/1998 |
| EP | 1 143 867 B1 | 11/1999 |
| JP | 61-109372 | 7/1986 |
| JP | 10-002316 | 1/1998 |
| JP | 11-512004 | 10/1999 |
| WO | 01/19264 | 3/2001 |

* cited by examiner

*Primary Examiner* — Thomas C. Barrett
*Assistant Examiner* — Sameh Boles
(74) *Attorney, Agent, or Firm* — Vidas, Arrett & Steinkraus, P.A.

(57) ABSTRACT

A fixation system for bones, with a connecting bar having plural through holes and at least one bone screw insertable into a through hole. The fixation system has at least one filler body, insertable into a through hole, and wherein the filler body is fastened in the through hole by having an overdimension with respect to the through hole.

10 Claims, 2 Drawing Sheets

BONE-FIXATION SYSTEM AND FILLER ELEMENT FOR BONE-FIXATION

CROSS-REFERENCE TO RELATED APPLICATIONS

Not applicable.

STATEMENT REGARDING FEDERALLY SPONSORED RESEARCH

Not applicable.

BACKGROUND OF THE INVENTION

The present invention is related to a fixation system for bones with a connecting bar having plural through holes and at least one bone screw, insertable into a through hole. Further, the present invention is related to a filler body for a fixation system of the aforementioned kind.

For the stabilisation of broken bones or of bone portions which are instable due to malunions or in the context of surgical cuts, a plate of metal with through holes and bone screws is used since 1886, following a proposal of C. Hansmann. This system has found worldwide acceptance. Today, it is the third important ostheosynthesis method besides to marrow nailing and ostheosynthesis by means of a fixateur externe.

The dimensioning of plate and bone screws, the proper selection of the metals for plate and bone screw with respect to its mechanical properties and its biocompatibility have been intensively investigated since this time by many research teams.

The importance of the non-positive fit between bone screw and plate has been increasingly recognised and implemented in the last 20 years. In the last years, the research of the present inventors has given the result that in a fixation system with plate and angle-stably fixed (i.e. not pivotal in the plate) screws—therefore a non-positive connection of bone screw and plate—the load on the plate is highest on the level of the first bone screw, which is adjacent to the instable bone portion. Thereafter, the load transmission decays further from through hole to through hole. Approximately, the bone screw in the first through hole transmits about 50 to 60% of the forces, the second bone screw about 20 to 30% and the third bone screw about 10 to 20%.

In order to take this fact into account, the solidity of the plate has been changed by adapted broadenings or thickenings of the plate on the level of the individual holes. This is described in WO 01/19264 A, the entire contents of which is incorporated herein by reference. This solution compensates the enfeeblement of the plate by the through hole. However, there is a demand to further improve the solidity of the plate.

Further, plates without broadenings or thickenings are continued to be used. In particular, in the context of the surgical repair of smaller bones, in the region of the hand skeleton for instance, such reinforcements of the plates in the region of the particularly stressed through holes are not advantageous, for reasons of the anatomic conditions. Therefore there is a demand to increase the solidity of plates otherwise, without broadenings or thickenings.

The same is correspondingly valid for other fixation systems, marrow nails for instance.

Departing from this, the present invention is based on the objective to provide or to make possible a fixation system with further or otherwise improved solidity.

BRIEF SUMMARY OF THE INVENTION

Advantageous embodiments of the fixation system and the filler body are indicated in the subclaims.

The fixation system for bones according to the present invention, with a connecting bar having plural through holes and at least one bone screw, which is insertable into a through hole, has at least one filler body, insertable into a through hole, and means for fastening the filler body in the through hole.

The filler body according to the present invention for a fixation system for bones, with a connecting bar having plural through holes and at least one bone screw, which is insertable into a through hole, is insertable into a through hole of the connecting bar and has means for fastening it in the through hole.

In the context of the present invention, it has been recognised that in many cases, a loss of the stability of fixation systems is due to the fact that a through hole of a connecting bar is not occupied by a bone screw. The non-occupation of through holes often takes place because the bone screw is interfering or superfluous. This happens regularly at long running fractures in particular or in the surgical repair of smaller bones with plates or other connecting bars without broadenings or thickenings. The enfeeblement is present with connecting bars having such reinforcements around the through hole as well as with connecting bars without them; however, it is particularly a problem with plates without such reinforcements. According to the present invention, a through hole not occupied by a bone screw is now filled up with a filler body, which increases the stability of this portion of the connecting bar, being equivalent to the screw head of a bone screw. By filling them up with a filler body, substantially the same stability as with inserted bone screw is achieved on through holes which are not occupied by a bone screw, and the stability of the fixation system as a whole is improved. The improvement is related to fixation systems with broadening or thickening of the connecting bar as well as to such ones without the same. The insertion and fastening of the filler body in the through hole can take place inside or outside the human body, as soon as it is decided which through holes are to be equipped with bone screws and which ones not.

In principle, filling the through hole with a filler body always leads to an increase of the stability of this portion of the connecting bar, irrespective of the realisation of the means for fastening the filler body in the through hole. Particularly high increases of the stability are achieved when the filler body is non-positively fastened on the wall of the through hole, by thread connection or material re-shaping, for instance. According to one embodiment, the filler body has therefore an outside thread and the through hole has an inside thread, into which the filler body is screwable with its outside thread. In this, the means for fastening are formed by the outside thread of the filler body and by the inside thread of the through hole. According to another embodiment with non-positive fastening of the filler body on the wall of the through hole, the filler body has an outside thread which can be mould into the through hole, and/or the through hole has an inside thread which is mouldable into the filler body. In this embodiment, the means for fastening are formed by the mouldable outside thread and/or the mouldable inside thread. In this, the filler body and the through hole are realised such as is described in detail in DE 43 43 117 C2 or EP 1 143 867 B1 for different realisations of the screw head and the through hole of fixation systems, for instance. The specifications concerning this in the two aforementioned documents are incorporated by reference into the present application. In both prior known realisations, an increase of the stability of the plate in the region of the filled through hole around 70 to 100% is achievable.

Realisations are also incorporated wherein the filler body has an outside thread and the through hole has an inside thread, which are screwable into each other without re-shaping, as well as those being connectable with each other via re-shaping and destruction of at least one thread.

According to one embodiment, the filler body has an overdimension with respect to the through hole. In this embodiment, the means for fastening are formed by the overdimension of the filler body in the through hole. The filler body can be fastened in the through hole for instance by pressing in the filler body, shrinking up the connecting bar or the like.

The embodiments with mouldable outside thread of the filler body and/or overdimension of the filler body are particularly suited for fixation systems (called "conventional fixation systems" hereinafter) in which the screw head of the bone screw does not have a fixed connection with the wall of the through hole. Suited for these conventional fixation systems is also a further embodiment, in which the filler body has plural filler body parts and a screw bridging the same for clamping the filler body in the through hole by contracting the filler body parts by means of the screw. In this, the means for fastening are formed by the plural filler body parts and the screw bridging the same.

This embodiment is also suited for filling up oblong through holes, which serve for the compression of the fracture gap. In this, the wall of the through hole is shaped such that there is an inclined plane. When turning in the bone screw, the spherical screw head wanders down the inclined plane and takes the bone fragment connected thereto with it, so that the bone fragments in the fracture gap are compressed. Suited for filling up oblong through holes are also correspondingly shaped filler bodies with an overdimension with respect to the through hole.

According to one embodiment, the filler body is an expansion body and has an expansion core insertable therein for expanding and clamping the expansion core in the through hole. In this, the means for fastening are formed by the expansion body and the expansion core insertable therein. This filler body is put into the through hole and fastened in it like a dowel. It is suited for angle-stable and for conventional fixation systems.

According to one embodiment, the filler body is made completely or partially from a material with memory effect, which is expandable by heat supply into its initial shape, by which it has a press fit in the through hole and/or the connecting bar and/or a positive connection with the through hole and/or the connecting bar. Thus, the filler body is fastened in the through hole by clamping and/or positive fit. This filler body is suited for angle-stable and for conventional fixation systems as well.

The press fit in the through hole can be effected by expanding the perimeter of the filler body in the through hole. The positive connection can take place by expanding the filler body up to abutment on two chamfers at the two ends of the through hole, or by lapping the outer sides of the connecting bar.

The material with a memory effect is a metal or a plastic material, for instance. The heat supply can take place by the body heat of the patient, for instance, or by selective local warming by means of a heating- or radiation device, respectively.

According to one embodiment, the filler body is formed from a material fillable into the through hole in its free-flowing state and being curable to a solid filler body in the plate hole. For instance, the cured material is a metal or a plastic material (polymethylmethacrylate, for instance). This filler body is fastened in the through hole by gluing and/or clamping and/or positive fit. It is suited for angle-stable and for conventional fixation systems as well.

According to one embodiment, the filler body and/or the through hole have roughened or other contact surfaces with an increased coefficient of friction. The fastening of the filler body in the through hole is supported or effected by frictional fit.

The following three embodiments increase the stability in the region of the through hole particularly well: according to one embodiment, the shape and the dimensions substantially correspond to the shape and dimensions of the through hole, so that it substantially fills up the through hole. According to a further embodiment, the means for fastening extend substantially over the complete wall of the through hole. According to a further embodiment, the filler body is made from a material having substantially the same rigidity as has the material of the connecting bar. Preferably, this is also valid for the rigidity of the material of the bone screw.

According to one embodiment, the filler body is made from metal and/or plastics. According to a further embodiment, the filler body is made from titanium or a titanium alloy.

According to one embodiment, the connecting bar is a plate. According to another embodiment, the connecting bar is a marrow nail.

According to a further embodiment, the connecting bar and/or the bone screw is made from titanium, a titanium alloy or another metal.

Finally, according to one embodiment, the filler body is made completely or at least in the region of contact to the connecting bat from a harder material than the connecting bar or at least than the region of contact of the connecting bar to the filler body, or reversely. The pairing of harder material and softer material at least for the contact regions of filler body and connecting bar is particularly advantageous for fastening means which have a moulding thread which is made from the harder material.

BRIEF DESCRIPTION OF THE SEVERAL VIEWS OF THE DRAWINGS

In the following, the present invention is explained in more detail by means of the attached drawing of realisation examples. In the drawings show.

DETAILED DESCRIPTION OF THE INVENTION

Figure 1:
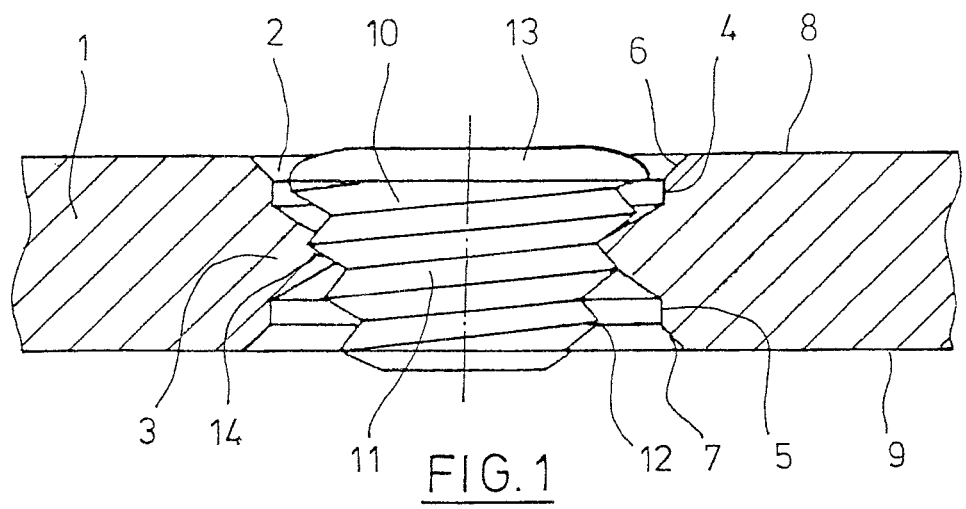
FIG. 1 a filler body in a through hole with a re-mouldable lip, in a vertical partial section.

While this invention may be embodied in many different forms, there are described in detail herein a specific preferred embodiment of the invention. This description is an exemplification of the principles of the invention and is not intended to limit the invention to the particular embodiment illustrated In the following discussion of different embodiments, coincident or substantially coincident features are indicated with the same reference numerals, which are provided with upstrokes for differentiation of the realisation examples.

According to FIG. 1, a plate 1 has a transversely directed through hole 2, in which about in the middle a re-mouldable lip 3 is arranged. Cylinder portions 4, 5 of the through hole 2 are adjacent to the lip 3. From on the outer ends of the cylinder portions 4, 5, the through hole 2 is enlarged towards the upside 8 and the downside 9 of the plate 1 by chamfers 6, 7.

In the through hole 2, a filler body 10 is arranged, which has a substantially conical thread portion 11 with an outside thread 12. On the end of the conical thread portion 11, having the greater diameter, the filler body 10 has a circulating annular bead 13.

On its topside, the filler body has a—not visible—tool engaging means, a slit for putting in the blade of a screwdriver, for instance.

The filler body and the plate 1 are made from titanium or a titanium alloy, for instance. Preferably, the filler body 10 is made from a harder material than the plate 1.

The filler body 10 is turned into the through hole 2 with the end of the conical thread portion 11 with the smaller diameter first. In doing so, the outside thread 12 moulds an inside thread 14 into the lip 3. The re-shaping force increases gradually, the filler body 10 seating more and more fast in the through hole 2. In the shown position, the filler body 10 stabilises the plate 1 in the region of the filler body 10.

Figure 2:
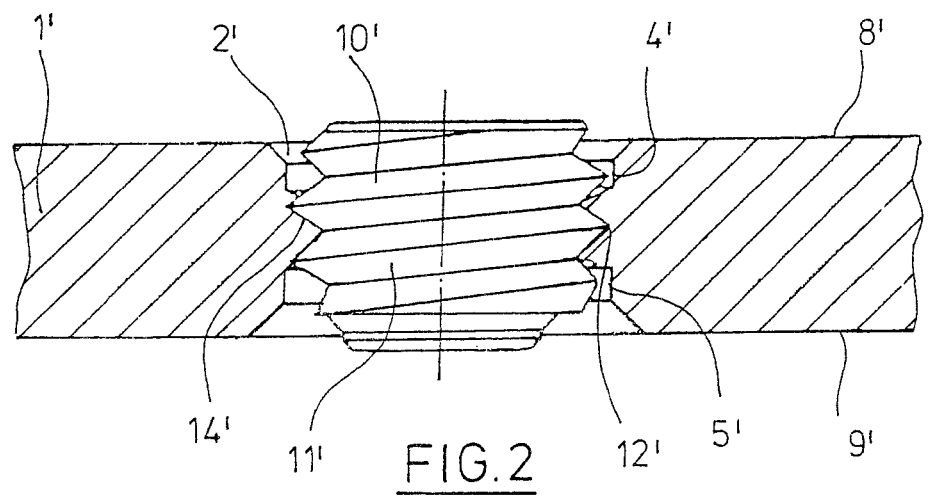
FIG. 2 a filler body in a through hole with an inside thread which is stronger moulded, in a vertical partial section.

The embodiment of FIG. 2 differs from the before described one substantially in that the filler body 10' has an approximately cylindrical thread portion 11' with faint decrease of the diameter towards both ends. The outer diameter of the outside thread 12' is always only faintly smaller than the inside diameter of the cylinder portions 4', 5' of the through hole 2' of the plate 1'. As a consequence, a more marked inside thread 14' is moulded in the lip 3' when the filler body 10' is turned in than in FIG. 1. Through this, the stability of the plate 1' in the region of the through hole 2' is further increased.

The decrease of the outer diameter of the thread 12' towards both ends facilitates the threading of the filler body 10' into the through hole 2' and the moulding of the inside thread 14' in the initial phase.

Figure 3:
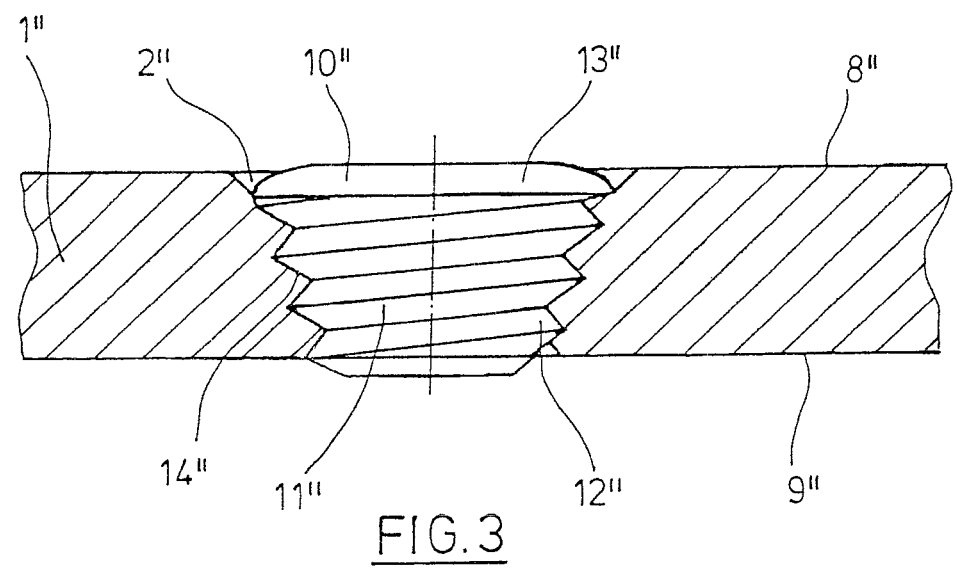
FIG. 3 a filler body in a through hole with an inside thread, in a vertical partial section.

According to FIG. 3, a through hole 2" is in a plate 1", which tapers from the upside 8" to the downside 9". In the through hole 2", an also gradually tapering inside thread 14" is present from the beginning.

A filler body 10" is turned into the plate 1", which is coincident with the filler body 10 of FIG. 1. The outside thread 12" of the filler body 10" is complementary to the inside thread 14".

The filler body 10" is screwed into the through hole 2" and clamped in it, due to the conical shape of the outside thread 12" and the inside thread 14". Because the filler body 10" is attached to or clamped with, respectively, the plate 1", over the whole wall of the through hole 2" approximately, the stability is particularly well increased in the region of the through hole 2".

Figure 4:
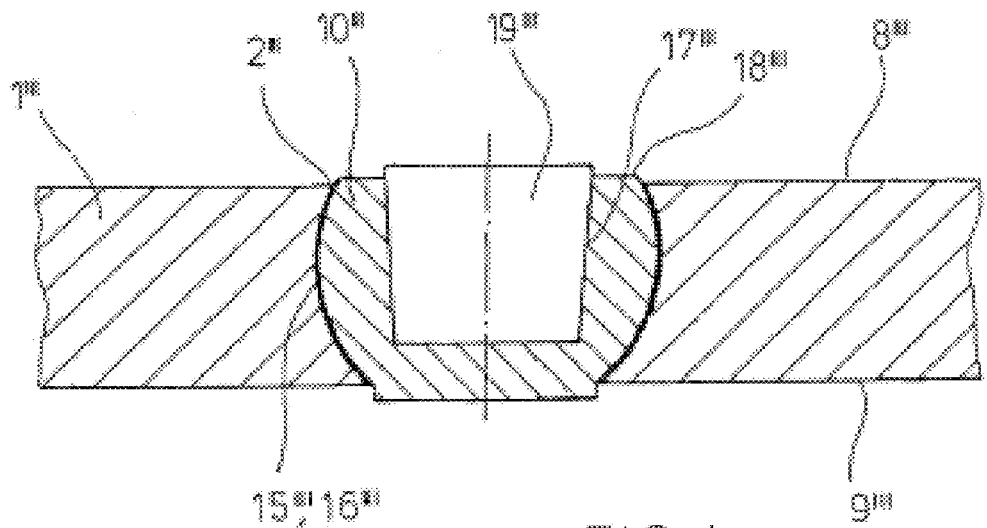
FIG. 4 a filler body formed as an expansion body in a through hole, in a vertical partial section.

According to FIG. 4, a plate 1''' has a through hole 2''' with a spherical dome shaped wall 15'''. A filler body 10''' formed as an expansion body is inserted into the through hole 2'''. The filler body 10''' has a spherical dome shaped cladding 16'''.

Further, the filler body 10''' has a blind hole 17''', which is opened towards its upside 18''' and tapers conically towards the same.

In the region of the blind hole 17''', the filler body 10''' has a slit in the axial direction. A conical expansion core 19''' is screwed into the blind hole 17'''. For this purpose, the blind hole 17''' has an inside thread and the expansion core 19''' has an outside thread, which engage one into the other. By screwing the expansion core 19''' into the blind hole 17''', the filler body 10''' is uniformly tensioned in the through hole 2''' and the stability increase of the plate 1'' is effected.

Figure 5:
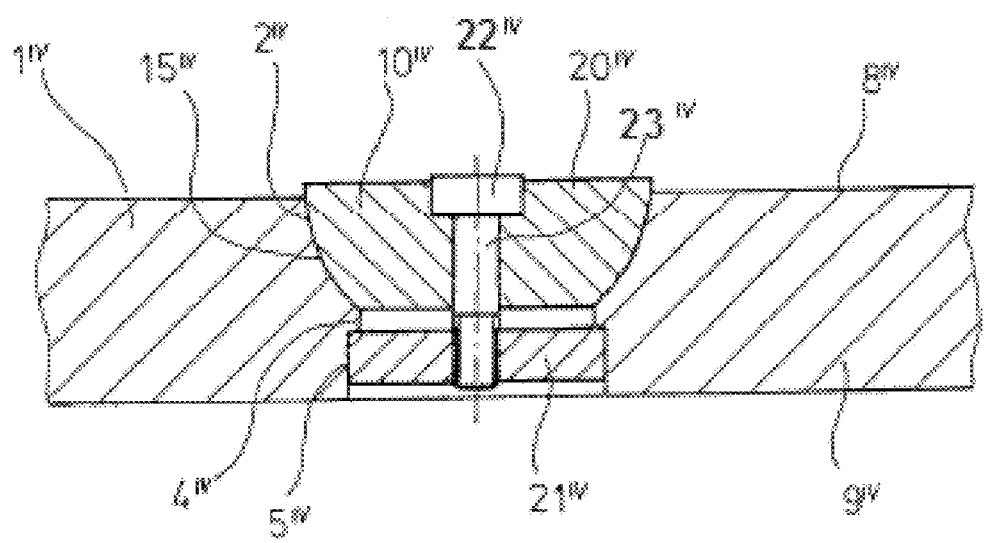
FIG. 5 a filler body with two filler body parts and a screw bridging the same in a through hole, in a vertical partial section.

According to FIG. 5, a plate $1^{IV}$ has a through hole $2^{IV}$ with an upper, dome-shaped wall $15^{IV}$ and a cylinder portion $4^{IV}$ adjacent thereto and a further cylinder portion $5^{IV}$ adjacent thereto, the inner diameter of which exceeds that one of the aforementioned cylinder portion $4^{IV}$.

The filler body $10^{IV}$ has a dome-shaped filler body part $20^{IV}$, which sits closely to the wall $15^{IV}$, and a cylindrical filler body part $21^{IV}$, which sits closely to the further cylinder portion $5^{IV}$. The filler body parts $20^{IV}$, $21^{IV}$ are braced with each other by a screw $23^{IV}$, which is supported by a screw head $22^{IV}$ on the topside of the filler body part $20^{IV}$, axially lead through the same and screwed into the filler body part $21^{IV}$, and thus clamped with the through hole $2^{IV}$. Through this, the stability in the region of the through hole $2^{IV}$ is increased.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

The invention claimed is:

1. Fixation system for bones, with a connecting bar having plural through holes and at least one bone screw insertable into a through hole, characterized in that it has at least one filler body, insertable into a through hole which is not occupied by a bone screw, and means for fastening the filler body in the through hole, further characterized in that the filler body has an overdimension with respect to the through hole such that the means for fastening are formed by the overdimension of the filler body in the through hole, and further characterized in that the filler body has an outside thread mouldable into the through hole and/or the through hole has an inside thread mouldable into the filler body.

2. Fixation system according to claim 1, characterized in that the filler body and/or the through hole have contact surfaces which are roughened or have otherwise an increased coefficient of friction.

3. Fixation system according to claim 1, characterized in that the shape and the dimensions of the filler body correspond to the shape and the dimensions of the through hole.

4. Fixation system according to claim 1, characterized in that the filler body is made from a material which has substantially the same rigidity as the material of the connecting bar.

5. Fixation system according to claim 1, characterized in that the filler body is made from metal and/or plastics.

6. Fixation system according to claim 1, characterized in that the filler body is made from titanium or a titanium alloy.

7. Fixation system according to claim 1, characterized in that the connecting bar is a plate.

8. Fixation system according to claim 1, characterized in that the connecting bar is a marrow nail.

9. Fixation system according to claims 1, characterized in that the connecting bar and/or the bone screw are made from titanium, a titanium alloy or another metal.

10. Fixation system according to claim 1, characterized in that the filler body is made completely or at least in the region of contact to the connecting bar from a harder material than the connecting bar or at least than the region of contact of the connecting bar to the filler body, or reversely.

* * * * *